United States Patent [19]
Noble

[11] Patent Number: 5,993,455
[45] Date of Patent: *Nov. 30, 1999

[54] SURGICAL BROACH AND METHODS FOR PREPARING THE MEDULLARY CAVITY OF A FEMUR IN HIP ARTHROPLASTY

[76] Inventor: Philip C. Noble, 2147 Swift Blvd., Houston, Tex. 77030

[*] Notice: This patent is subject to a terminal disclaimer.

[21] Appl. No.: 08/749,281

[22] Filed: Nov. 13, 1996

[51] Int. Cl.⁶ .................................................. A61B 17/56
[52] U.S. Cl. .............................................. 606/85; 606/79
[58] Field of Search .................. 606/85, 80, 84, 606/79, 96, 89, 87, 86, 99, 100

[56] References Cited

U.S. PATENT DOCUMENTS

| | | | |
|---|---|---|---|
| 4,306,550 | 12/1981 | Forte | 606/85 |
| 4,552,136 | 11/1985 | Kenna | 606/85 |
| 4,587,964 | 5/1986 | Walker et al. | 606/85 |
| 4,601,289 | 7/1986 | Chiarizzio et al. | |
| 4,738,256 | 4/1988 | Freeman et al. | |
| 4,765,328 | 8/1988 | Keller et al. | |
| 4,777,942 | 10/1988 | Frey et al. | |
| 4,809,689 | 3/1989 | Anapliotis | |
| 5,006,121 | 4/1991 | Hafeli | 606/85 |
| 5,047,033 | 9/1991 | Fallin | |
| 5,169,401 | 12/1992 | Lester et al. | |
| 5,169,402 | 12/1992 | Elloy | |
| 5,454,815 | 10/1995 | Geisser et al. | 606/85 |

FOREIGN PATENT DOCUMENTS

| | | |
|---|---|---|
| 27 32 325 | 1/1979 | Germany . |
| 195 01 882 | 11/1995 | Germany . |
| 2 250 441 | 6/1992 | United Kingdom . |
| WO 94/27507 | 12/1994 | WIPO . |
| WO 96/17553 | 6/1996 | WIPO . |

OTHER PUBLICATIONS

"The S–ROM™ Total Hip System"—Joint Medical Products product brochure (8 pages); 1989.
"Impact Moduler Total Hip System"—Biomet product brochure (19 pages); 1992.
"Porous–Coated Femoral Component Surigal Technique"—Smith Nephew Richards product brochure (28 pages); undated.

Primary Examiner—Michael Buiz
Assistant Examiner—David O. Reip
Attorney, Agent, or Firm—Laura Barrow

[57] ABSTRACT

A machining assembly, including a novel broach design, are disclosed for preparing a femoral medullary cavity for receipt of a femoral prosthetic stem, wherein the configuration of the implantation site allows for the neutral alignment of the prothesis within the medullary cavity for improved rigid fixation of the prosthetic stem therein. Aspects of the inventive machining assembly include a novel broach comprising a proximal lateral recess that allows for initial avoidance of the greater trochanter during implantation, thereby resulting in the preparation of a neutrally aligned cavity with respect to the broach. The machining assembly also includes a means for subsequently removing the bone of the greater trochanter once neutral alignment between the medullary cavity and broach are achieved for the subsequent implantation of a neutrally aligned femoral prosthesis.

7 Claims, 14 Drawing Sheets

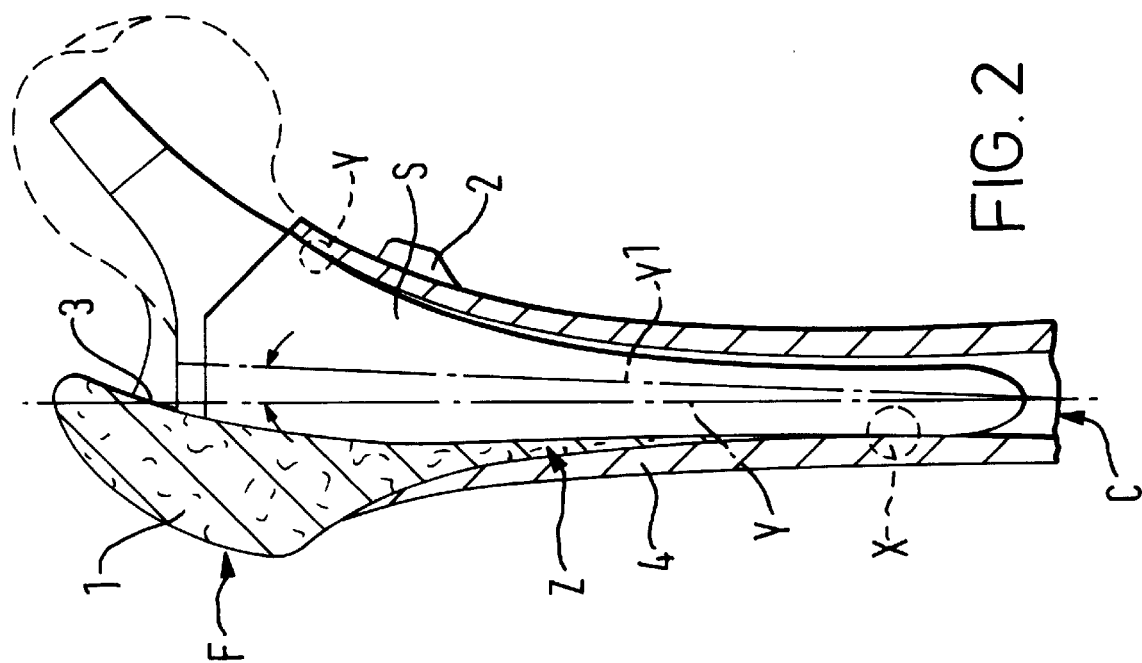

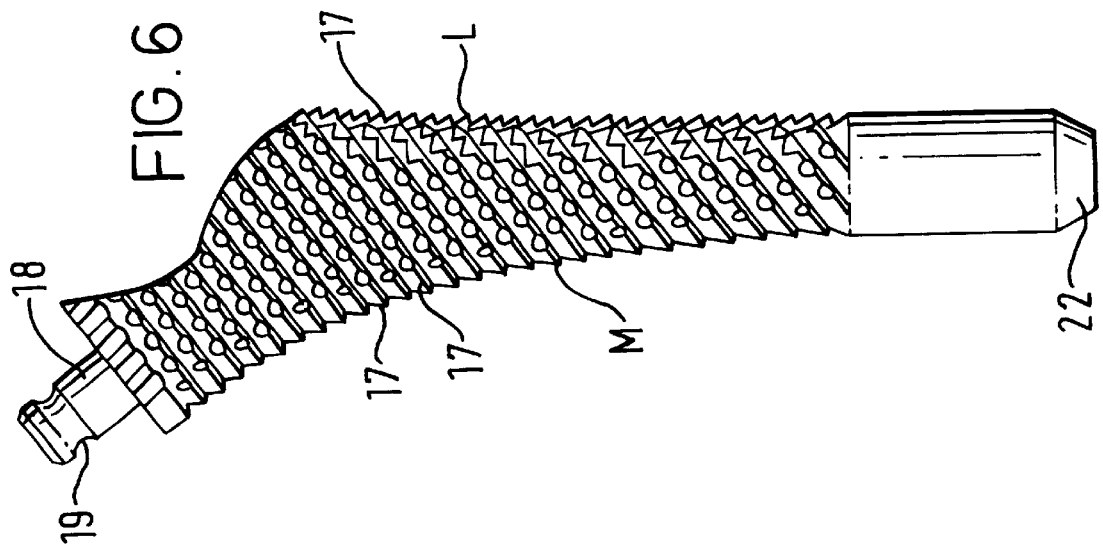
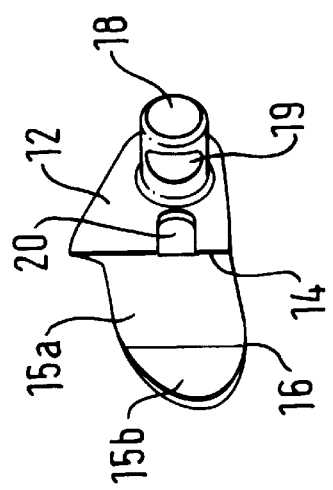
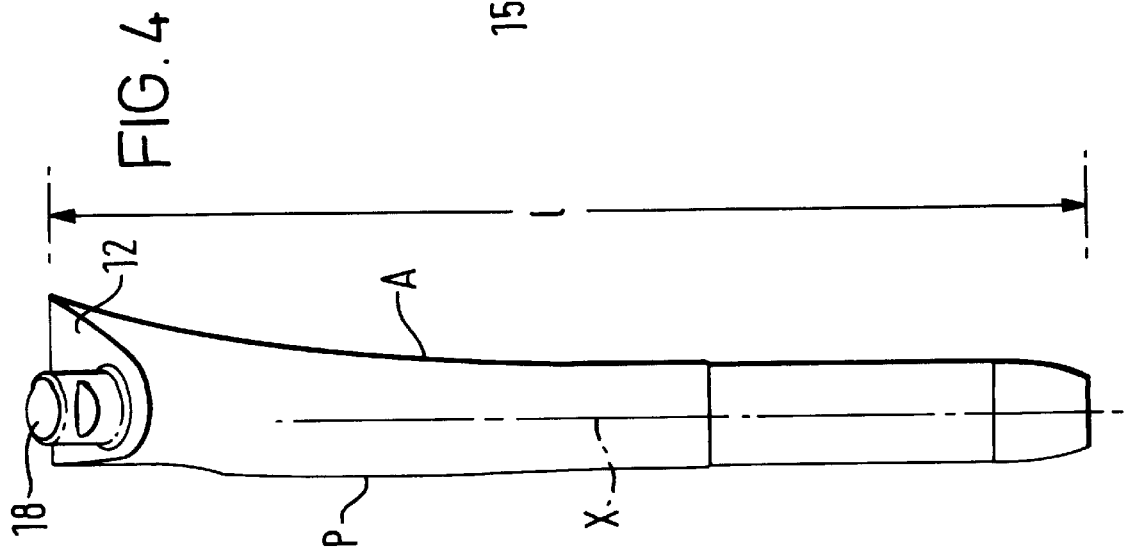

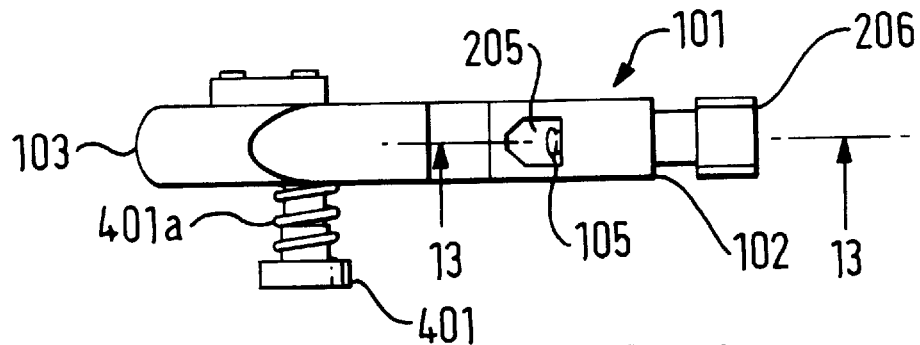
FIG. 12
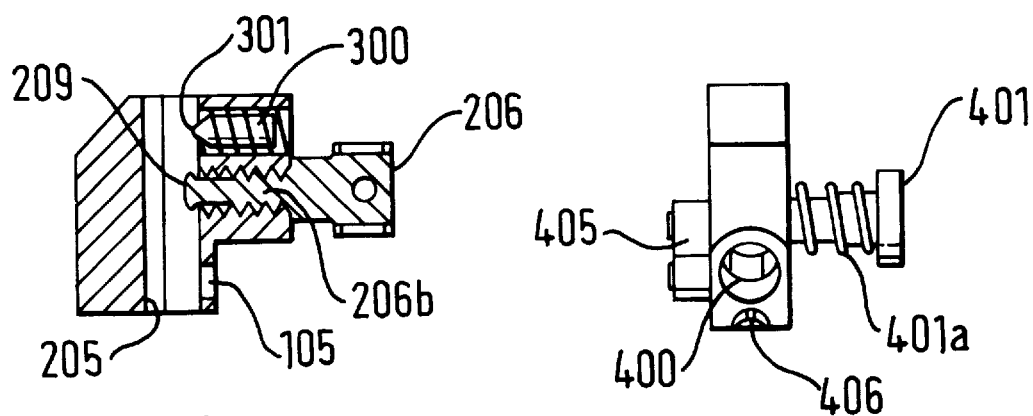
FIG. 13
FIG. 14
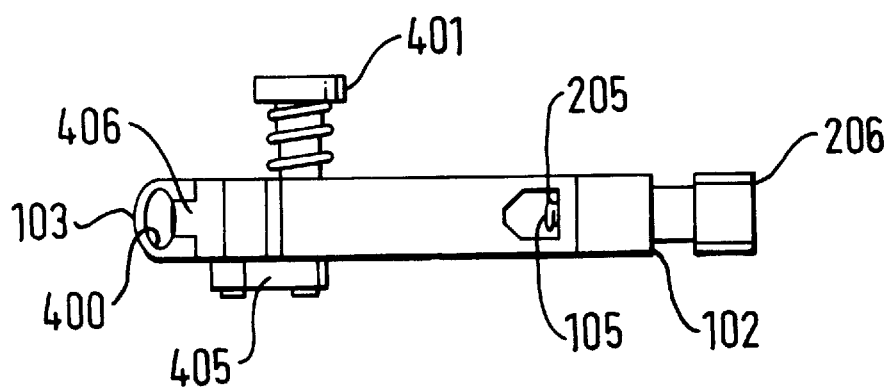
FIG. 15

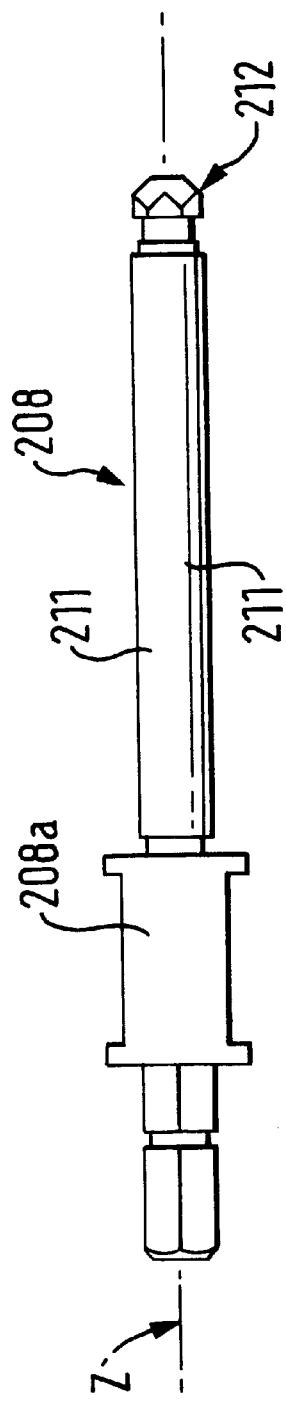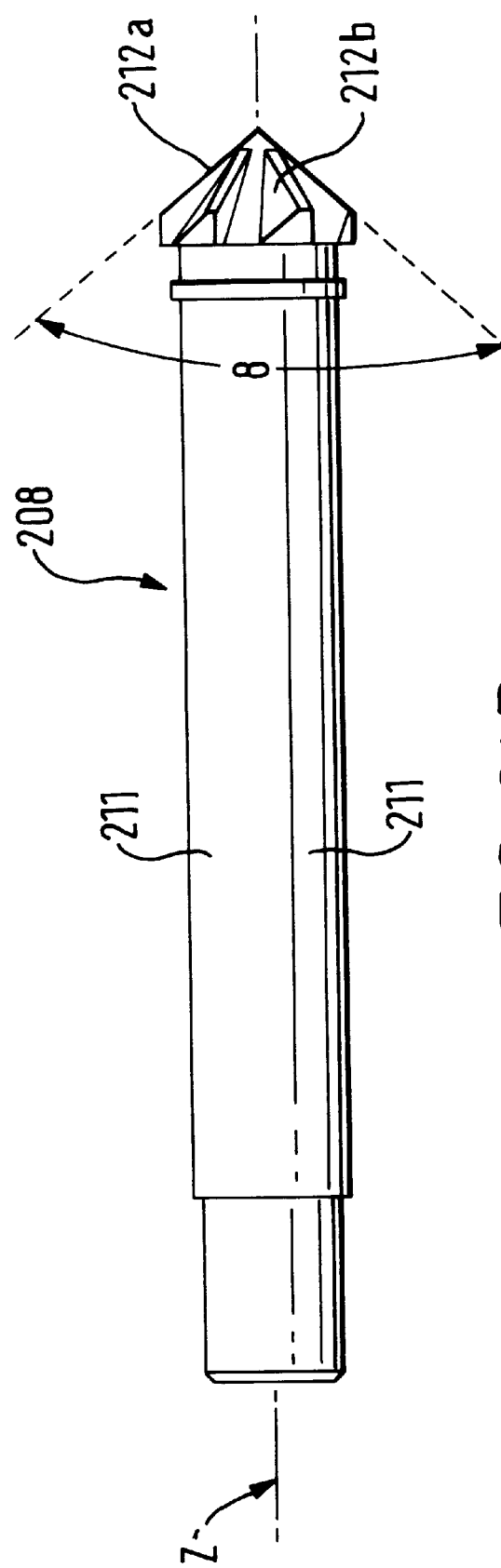
FIG. 24A
FIG. 24B

SURGICAL BROACH AND METHODS FOR PREPARING THE MEDULLARY CAVITY OF A FEMUR IN HIP ARTHROPLASTY

BACKGROUND OF INVENTION

The present invention relates to a broach and method for preparing a medullary cavity for receiving a stem component of a femoral prosthesis, specifically an improved machining assembly and method for preparing a medullary cavity that allows for the implantation of a femoral prosthesis that is neutrally aligned within the prepared medullary cavity for improved fixation therein, thereby minimizing any subsequent loosening and pain commonly associated with mis-aligned prostheses.

It is widely known that the success of cementless hip replacement depends on correct sizing and placement of prosthesis within the medullary cavity of the femur. In cases that fail due to aseptic loosening, a common observation is that the implant is not large enough to achieve support through filling the implant site and thereby achieving contact with the cortical surfaces of the femur. Typically, these undersized prostheses are mis-aligned and have been placed in some degree of varus inclination with respect to the medullary axis of the femur. Consequently, the implant only achieves contact with the cortex of the femur medially, immediately below the surface of the proximal femoral osteotomy, and laterally, adjacent to the distal tip of the prosthetic stem. However, contact is not present in other areas, including the anterior and posterior cortices, the medial cortex beneath the lesser trochanter, or the lateral cortex above the distal tip of the implant. Contact in these areas is necessary to rigidly fix the prosthesis and to prevent excessive relative motion at the implant/bone interface which would lead, ultimately, to pain and loosening.

In practice, prostheses that are implanted in the femur are undersized because the opening formed by the surgeon does not extend far enough laterally within the proximal femur to allow the prosthesis to be aligned with the longitudinal axis of the canal. This occurs because the medullary axis passes through the superior surface of the femur in the vicinity of the medial edge of the greater trochanter, close to the posterior cortex of the femoral neck, in an area of strong bone which is difficult to machine using conventional instruments, including broaches, rasps, and reamers. As the bone adjacent to this area is relatively soft, conventional machining instruments tend to be deflected away from the hard bone and enter the medullary canal at a site that is located more anteriorly and medially. As subsequent instruments enlarge the initial point of entry, bone is progressively removed from the anterior and medial walls of the cavity, leading to the development of a mis-aligned implantation site.

If a broach or rasp is placed into a femoral canal through an entry hole that is not aligned with the medullary axis, the broaching or rasping instrument will become wedged in the canal because the teeth present on the devices are generally incapable of effectively removing areas of hard bone which block their advancement. Removal of this bone, generally, can only be effected by rotating machine tools, such as flexible or rigid reamers or, possibly, bone chisels. Thus, in conventional hip replacement, preparation of a neutrally-aligned implantation cavity depends critically upon the initial entry point of instruments into the femur and the use of adjunctive instruments to machine away the areas of hard bone that block the motion of the broach as it seeks to achieve neutral alignment within the canal.

The anatomic variability of the proximal femur also contributes to mis-alignment and undersizing of femoral prostheses. The medullary axis panes through the superior surface of the femur at a point that varies by +/-5 mm medial-laterally and anterior-posteriorly, the precise location depending upon the shape of the metaphysis and the orientation of the femoral neck with respect to the rest of the femur. For this reason, it is difficult to determine intraoperatively whether instruments placed in the femoral canal are correctly aligned and whether the entry point for instruments designed to machine the femur is situated sufficiently laterally and posteriorly to allow development of a neutrally aligned implantation site.

The conventional approach to minimizing the difficulties in preparing the femur in the presence of areas of hard bone has been to insert a reaming instrument, typically a long, conical reamer or medullary drill, into the medullary cavity and to assume that the instrument would be co-axial with the medullary cavity during its insertion, in effect forcing the proximal part of the instrument to cut into the greater trochanter to an extent necessary to provide correct alignment of the prepared cavity. In practice, this approach has not been entirely successful because of the following factors:

(1) The bone within the trochanter is generally very hard, greasy, and often covered with a considerable quantity of soft tissue which tend to impair the cutting action of conventional drilling and reaming instruments.

(2) This approach assumes that the instrument will be aligned with the medullary cavity without enlarging or cutting the bone distally, thereby distorting the cavity itself. In practice, the use of long drills and instruments that are not smooth-tipped can lead to mis-alignment because the instrument cuts bone both proximally and distally.

(3) The entire approach of using the intramedullary cavity to guide the alignment of instruments assumes that the diaphyseal and metaphyseal segments of the femur coincide. In practice, however, there is a deviation of up to two degrees between the axis of the metaphysis and the diaphysis of the medullary cavity. Consequently, the path machined by the distally-guided instrument only gives a rough indication of where a neutrally-positioned instrument should lie within the metaphysis.

(4) Aggressive reaming instruments and drills often remove a considerable segment of the greater trochanter during their insertion. This necessitates greater exposure of the surgical site and removal of excessive bone, and may lead to increased long-term osteolysis as soft cancellous bone is exposed to wear debris generated within the joint.

There exist many devices that assist the process of shaping the femoral canal to match the contours of the femoral implant; however, the successful function of each of these devices is predicated on the assumption that some instrument has been inserted into the medullary canal in a neutral position. Such an instrument is then used as a platform for locating reamer guides of a variety of designs. Such instruments have been available commercially and are primarily used to facilitate reaming of the medial bone within the femur, which is often very strong and may prevent the use of a correctly sized prosthesis. Exemplary instruments are manufactured by Biomet, Inc. (Warsaw, Ind.) and are also disclosed in U.S. Pat. No. 4,809,689 (Anapliotis), U.S. Pat. No. 4,777,942 (Frey, et al.), and U.S. Pat. No. 4,738,256 (Freeman et al.).

Additional instrument designs are available for use with modular prostheses comprising interchangeable anterior and posterior elements which are mounted on the central stem of the prosthesis. The Richards Medical Company (Memphis, Tenn.) manufactures a system consisting of a plurality of modular reaming guides that utilize a rail attached to a stent placed in the medullary canal. The function of the rail is to guide the position of the reamer used to machine both the anterior and posterior surfaces of the femur to optimize the fit of this prosthesis within the femur.

Another design is disclosed in U.S. Pat. No. 5,169,402 (Elloy) and comprises a broach having two separate parts that connect on a articulating handle to form a solid, uniform piece. The smaller segment of the original broach consists of the medial part of the broach, extending down from the upper face of the osteotomy level. This segment is spring-loaded so that as the surgeon drives the broach into the femur, the medial segment gets caught at some point within the medial cortex. Consequently, as the surgeon advances the body of the instrument further down the femur, the medial segment slides along a track present in the body and remains in a position protruding from the bone. The motion of the segment is constrained by a spring, so that once the rest of the broach has become seated in the bone, the surgeon may drive the medial segment alone into place within the femur, thereby completing the machining operation to form the implantation cavity.

SUMMARY OF INVENTION

The present invention is directed in certain aspects to an improved broach design and method for preparing a medullary cavity of a femur for subsequent implantation of a neutrally aligned femoral prosthesis. Specifically, the broach includes a longitudinal axis and anterior, posterior, medial, and lateral faces. The overall configuration of the broach is similar to that of many femoral stem components medially, distally, and in the mid-shaft region. However, in the proximal region, the broach has a recess that is positioned on the lateral face and extends from the superior end of the broach downward of the proximal segment. More specifically, the recess comprises a medial portion and a distal portion, wherein the medial portion is spaced medially from the lateral face and extends distally from the superior end to the distal portion, and the distal portion extends laterally from the medial portion to the lateral face. In the most preferred embodiment, this recess extends across the entire lateral face of the broach (i.e. from the anterior face to the posterior face), as opposed to just a portion of the lateral face (i.e. the posterior/lateral corner). The configuration of the recess permits the broach, upon implantation into the medullary cavity of the femur, to avoid the strong bone of the greater trochanter. Initial avoidance of this region of strong bone is important in order to achieve a desired shape of the medullary cavity for receipt of a femoral stem, since conventional instruments are often deflected away from this bone area during the machining process, thereby resulting in a prepared cavity having a shape that will not allow for the desired neutral alignment of the prosthesis therein. In the present invention, avoidance of this region due to the presence of the proximal lateral recess allows the inventive broach to be seated within the medullary cavity such that the longitudinal axis of the broach substantially coincides with the medullary axis to achieve neutral alignment. Consequently, upon subsequent removal of a sufficient amount of trochanteric bone to allow implantation of a femoral stem prosthesis (or a finishing broach prior to implantation of the prosthesis), the femoral prosthesis is able to achieve neutral alignment within the medullary cavity upon implantation.

More specifically, the present invention is directed to the use of the inventive broach in combination with a novel machining device including a second cutting instrument, the device being designed to remove areas of bone initially avoided by the inventive broach, especially bone from the greater trochanter and the posterior/lateral corner of the osteotomy site, to allow for subsequent implantation of a femoral prosthesis or broach.

BRIEF DESCRIPTION OF THE DRAWINGS

The objects, advantages, and features of the invention will become more apparent by reference to the drawings which are appended hereto, wherein like numerals indicate like parts and wherein an illustrated embodiment of the invention is shown, in which:

FIG. 1 is a posterior view of a neutrally aligned prosthesis implanted within a femur.

FIG. 2 is a posterior view of a mis-aligned prosthesis implanted within a femur.

FIG. 4 is medial view of the inventive broach.

FIG. 5 is a top plan view of the inventive broach.

FIG. 6 is an anterior view of a left component of one embodiment of the partial broach illustrating the positioning of the preferred cutting teeth.

FIG. 12 is a medial view of the machining assembly (without the broach and second cutting instrument).

FIG. 13 is a cross-section view of the machining assembly taken along lines 13—13 of FIG. 12 illustrating the preferred means for securing the guide to the mounting block.

FIG. 14 is a bottom plan view of the machining assembly (without the broach and second cutting instrument).

FIG. 15 is a lateral view of the machining assembly (without the broach and second cutting instrument).

FIGS. 24A–24B are side views of the preferred second cutting instrument component of the machining assembly.

DETAILED DESCRIPTION OF THE PREFERRED EMBODIMENTS

I. Partial Broach Design and Method

Figure 3:
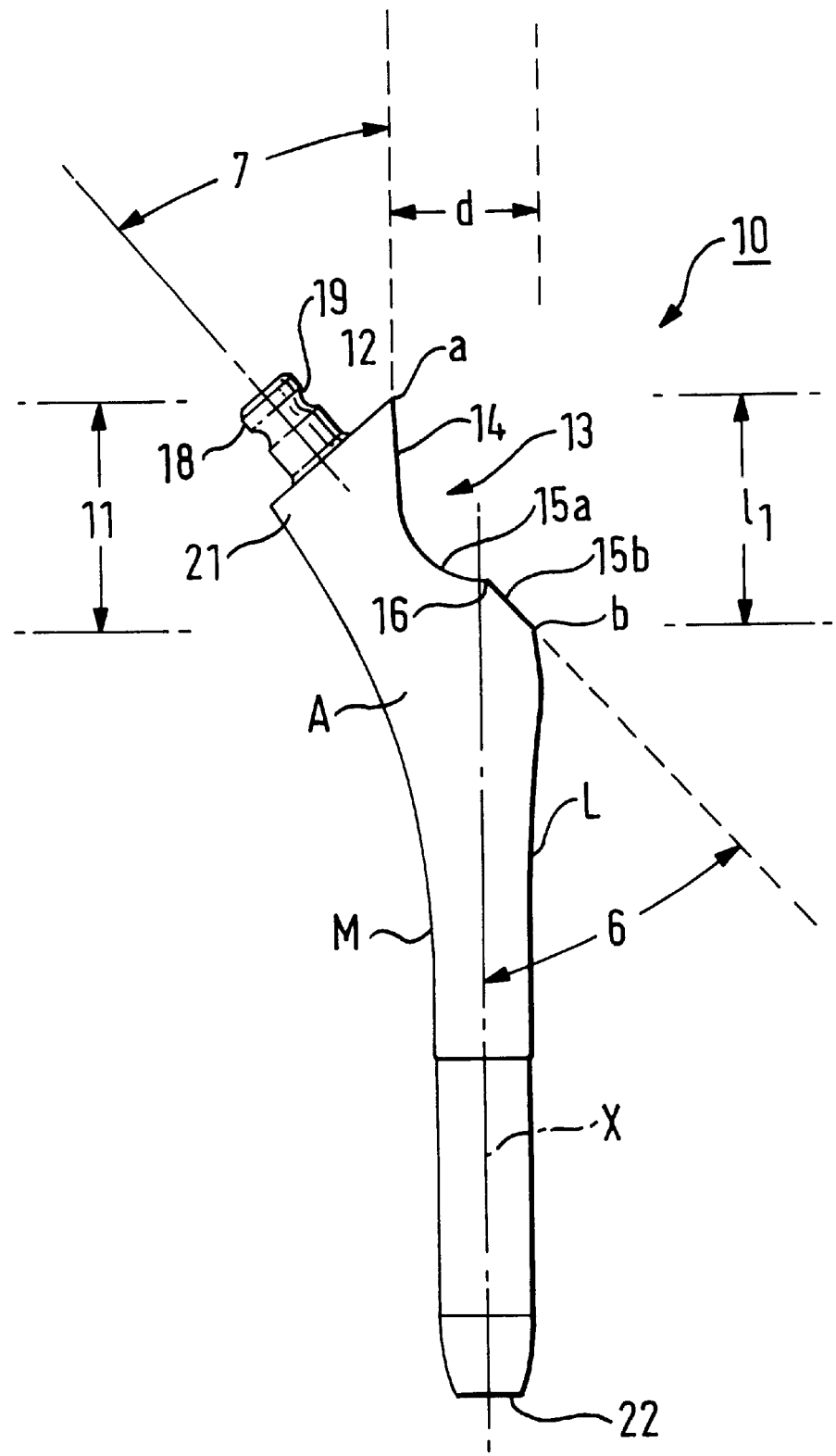
FIG. 3 is an anterior view of a left component of the inventive broach.

The present invention is directed to an improved broach design and method for preparing the medullary cavity of a femur for subsequent implantation of a femoral prosthesis in hip arthroplasty. After the medullary cavity is prepared using the inventive broach, a femoral stem component of a hip prosthesis may then be implanted within the cavity, wherein the longitudinal axis of the stem is in neutral alignment with the medullary axis of the femur, resulting in improved rigid fixation of the stem, thereby minimizing the possibility of future loosening of the implant and pain associated with such loosening. The phrase "neutral alignment" as used herein refers to the substantial coincidence of longitudinal axes, specifically the medullary axis of the femur and the longitudinal axis of the broach or femoral prosthesis, as discussed in further detail below.

When preparing the implantation site within the medullary cavity, it is desirable that the site be configured such that upon implantation of the femoral prosthesis, full contact is achieved between the outer surface of the stem and the surface of the cavity. As illustrated in FIG. 1, such contact is achieved when the stem (S) is placed in neutral alignment within the medullary cavity (C) (i.e. the longitudinal axis ($Y^1$) of the stem (S) and the medullary axis (Y) of the femur (F) substantially coincide). FIG. 2 illustrates an undesirable implantation due to inaccurate broaching of the cavity where only partial contact is achieved between the stem (S) and the medullary cavity (C) (as shown in circled areas x and y). In addition, a gap is present between the stem (S) and the lateral cortex (4) in the region (z). Consequently, such broaching has resulted in misalignment of the stem (S) wherein the longitudinal axis ($Y^1$) of the stem (S) is placed in some degree of varus alignment (5) with respect to the medullary axis (Y) of the femur.

As discussed above, a problem that often occurs during conventional broaching/rasping is that the cutting instrument is deflected away from the hard bone of the greater trochanter (1), especially in the vicinity of the posterior margin of its medial wall (3), where the bone is generally very difficult to machine with conventional instruments, thereby altering the path of the instrument towards the softer adjacent bone at a site that is located more anteriorly and medially. As subsequent cutting instruments enlarge the initial point of entry, the bone is progressively removed from the anterior and medial walls of the cavity, leading to the development of a mis-aligned implantation site.

The present invention is directed to a broach design and method for preparing the implantation site within the medullary cavity to allow for neutral alignment of a subsequently implanted femoral stem prosthesis, namely by employing a design that allows the broach to avoid the greater trochanter during initial broaching and preparation of the implantation site. Referring now to FIGS. 3–6A, the present invention comprises a partial broach (10) having a longitudinal axis (X) defining anterior (A), posterior (P), medial (M), and lateral (L) faces, a plurality of teeth (17) positioned on at least one the faces (shown in FIGS. 6, 6A, and 7) and a lateral recess (13) positioned on the proximal segment (11) (i.e. about upper one-third) of the broach. While the smallest recess should occupy the posterior/lateral corner of the broach (not shown) to avoid the bulky region of the greater trochanter, the most preferred embodiment comprises a lateral recess (13) that extends from the anterior face (A) to the posterior face (P), as shown in the figures. It should be further noted that while the description of the invention and the related figures are directed to a left femoral broach, the present invention may also be designed for a right broach, which is merely a mirror image of the left broach described and illustrated herein.

FIGS. 3–6A illustrate a preferred configuration of the recess (13); however, alternative configurations of the recess may be employed, provided that each are of sufficient depth and proper placement to allow the broach to avoid the desired bony area, typically the greater trochanteric region of the femur. FIGS. 3 and 5, for example, illustrate a preferred lateral recess design which is substantially concave and comprises, in a series, a substantially flat medial portion (14) (extending distally from about point a of the superior end (12)) and a distal portion extending laterally from the medial portion. The distal portion further includes a chamfer (15b) extending distally from a lateral edge (16) to about point b and preferably positioned at an angle (6) of about 30 to about 60 degrees, most preferably about 45 degrees, relative to the longitudinal axis (X) of the broach. The chamfered edge (15b) of the recess is a preferred design feature that allows the broach (10) to avoid impingement against lateral bone beneath the greater trochanter, thereby minimizing the chance of a fracture upon extraction of the broach from the femur.

Figure 6A:
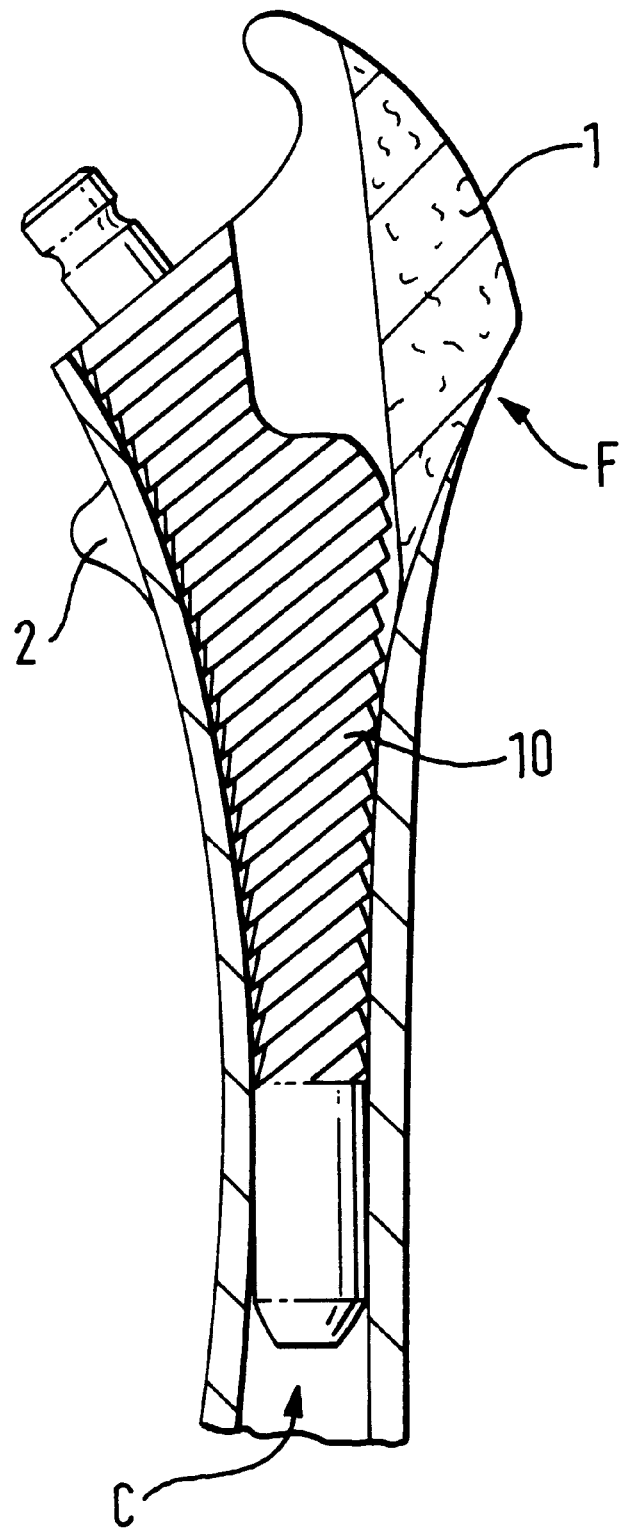
FIG. 6A is an anterior view of the left component of another embodiment of the inventive broach illustrating the broach implanted within the medullary cavity of a femur.

As illustrated in FIGS. 6–6A, the inventive broach comprises a plurality of cutting teeth (17) positioned on at least the medial face (M), but most preferably on all four faces of the broach (10). The configuration of the cutting teeth may be the same on all of the faces; however, the most preferred types and arrangement of cutting teeth are those shown in FIG. 6 as well as those described and illustrated in co-pending application Ser. No. 08/594,892 and which is incorporated by reference herein in its entirety. While the preferred embodiment of the broach described in Ser. No. 08/594,892 comprises a plurality of aggressively cutting diamond-shaped teeth on the lateral face, the presence of a lateral recess on the partial broach minimizes the need for aggressive cutting of lateral bone.

Figure 3A:
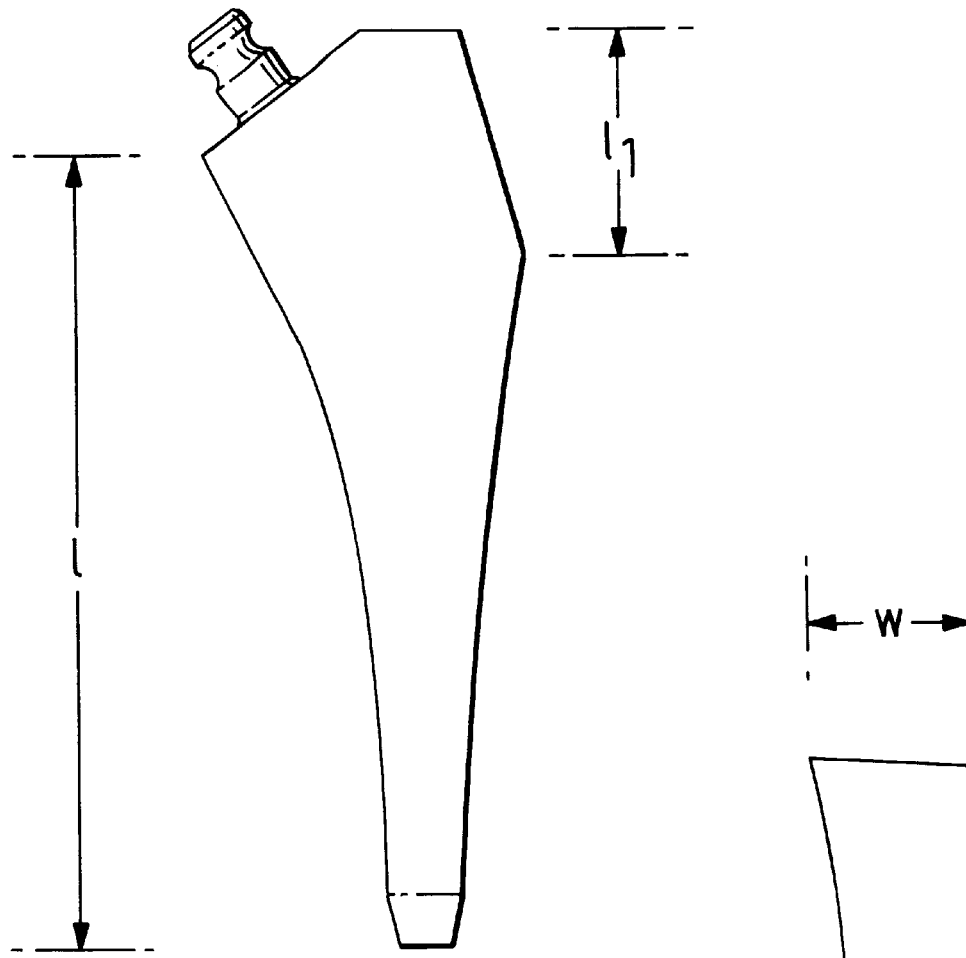
FIG. 3A is an anterior view of a full broach used to construct the partial broach.
Figure 3B:
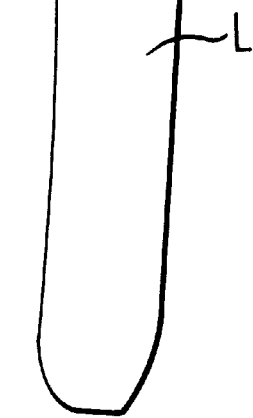
FIG. 3B is a lateral view of the full broach illustrated in FIG. 3A.

In the preferred embodiment, the inventive partial broach is prepared from a "full" broach (i.e. one not having a lateral recess), as illustrated in FIGS. 3A and 3B, whereby the recess portion is cut out of the full broach. Preferably, the material is removed from the proximal lateral face of the broach such that the "length" of the recess ($l_1$) (see FIGS. 3 and 3A) is from about 1.0 inch to about 1.2 inches, most preferably about 1.125 inches. Moreover, the preferred depth (d) of the recess, as illustrated in FIG. 3, is from about 0.80 inches to about 1.3 inches, with the preferred radius of the concavity (the concavity (15a) being generally positioned where the medial and distal portions of the recess meet) ranging from about 0.35 inches to about 0.70 inches, most preferably from about 0.500 to about 0.625 inches.

Table 1 lists the preferred depths (d) of the recess and size of the concavity radius for particular broach sizes.

The inventive broach may be supplied in a range of different sizes to meet different surgical requirements. Table 2 lists preferred widths (w) and longitudinal lengths (l) for particular broach sizes. The width (w) values are obtained from a full broach (FIG. 3B) measured from the anterior face to the posterior face. Moreover, in the coronal plane, the neck (21) of the broach is positioned at an angle (7) relative to the broach's longitudinal axis (X) of about 36 degrees, as illustrated in FIG. 3. Preferably, the overall configuration of the broach is the same as the configuration of the femoral prosthesis employed (except for the lateral recess). The figures illustrate an asymmetric design wherein the broach possesses a sight posterior bow, as best illustrated in FIG. 4.

TABLE 1

| Broach size | Depth (d) (inches) | Radius (inches) |
| --- | --- | --- |
| No. 2 | 0.897 | 0.500 |
| No. 3 | 1.010 | 0.500 |
| No. 4 | 1.120 | 0.625 |
| No. 5 | 1.221 | 0.500 |
| No. 6 | 1.290 | 0.625 |
| No. 7 | 1.283 | 0.625 |
| No. 8 | 1.277 | 0.625 |

TABLE 2

| Broach size | Length ($l_1$) (inches) | Width (w) (inches) |
| --- | --- | --- |
| No. 2 | 4.699 | 0.704 |
| No. 3 | 4.863 | 0.757 |
| No. 4 | 5.019 | 0.827 |
| No. 5 | 5.164 | 0.878 |
| No. 6 | 5.395 | 0.949 |
| No. 7 | 5.347 | 1.002 |
| No. 8 | 5.667 | 1.068 |

II. Surgical Method of Using the Partial Broach

The inventive broach (10) is generally used in conjunction with a drill or awl (not shown) which is utilized to form an entry hole in the superior cortex of the femoral neck, preferably in the vicinity of the exit point (3) of the medullary axis (Y) (see FIGS. 1 and 2). Once a hole has been made that is large enough to accommodate the distal tip (22) of the broach, a detachable handle (not shown) is rigidly attached to the superior surface of the broach which is then driven into the femur (F) with a mallet or similar instrument. As the broach is advanced down the femur, it will generally rotate until contact is achieved with the medial cortex proximally and the lateral femoral cortex just below the level of the lesser trochanter (2). If necessary, a succession of broaches or rasps of increasing size may be passed down the femur until a rigid fit is achieved at the appropriate position within the femur to allow optimal reconstruction of the femoral head center. At this point, an intimate fit will be achieved between the broach and the medullary cavity, and consequently the longitudinal axis (X) of the broach (10) and the medullary axis (Y) will substantially coincide (i.e. be in neutral alignment).

Once the femur has been prepared using the inventive broach, inventive broach (10) is removed from the medullary cavity. Next, a second finishing broach may be implanted in the medullary cavity of the femur to enlarge the implantation site to its final shape. Since generally the finishing broach is minimally larger than the inventive broach, with the exception of the recessed area, all of the energy delivered to the finishing broach can be utilized solely in removing bone in the medial aspect of the greater trochanter, which was initially avoided by the partial broach. The finishing broaches with cutting teeth of conventional diamond-shaped configuration can be readily implanted in a neutral orientation, provided that the implantation cavity has been initially prepared with the inventive broach.

III. Machining Assembly

Figure 7:
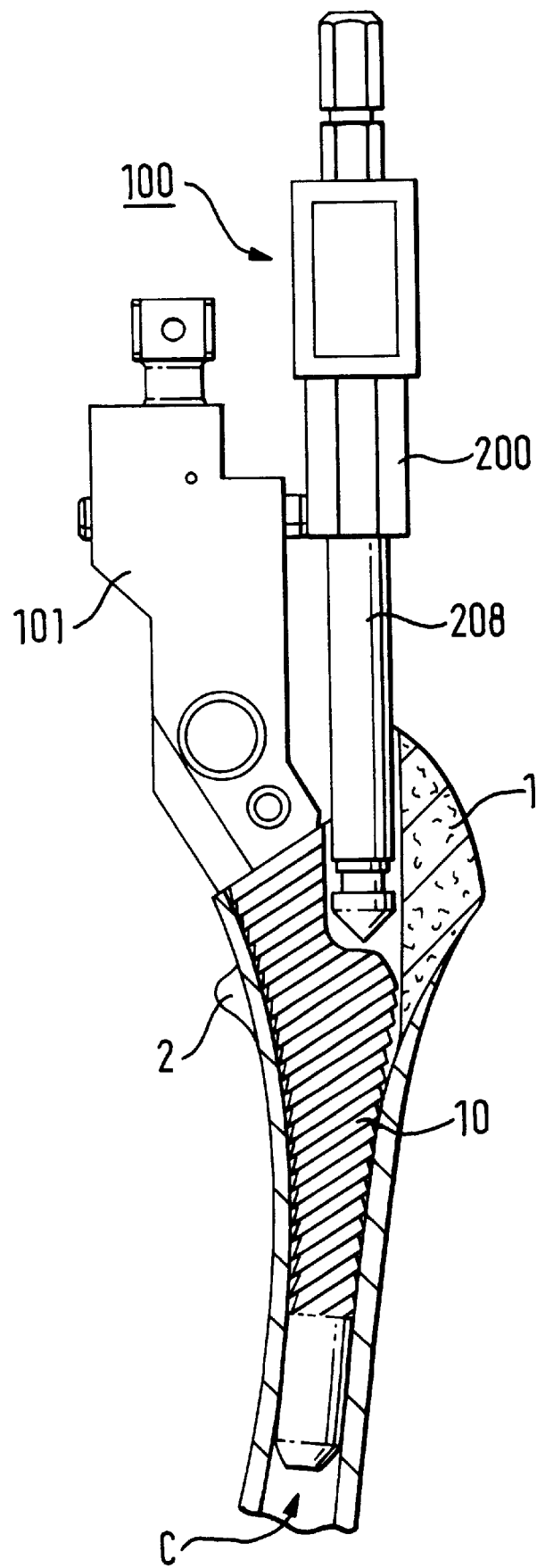
FIG. 7 is an anterior view of the inventive machining assembly implanted within the medullary cavity of a femur.
Figure 8:
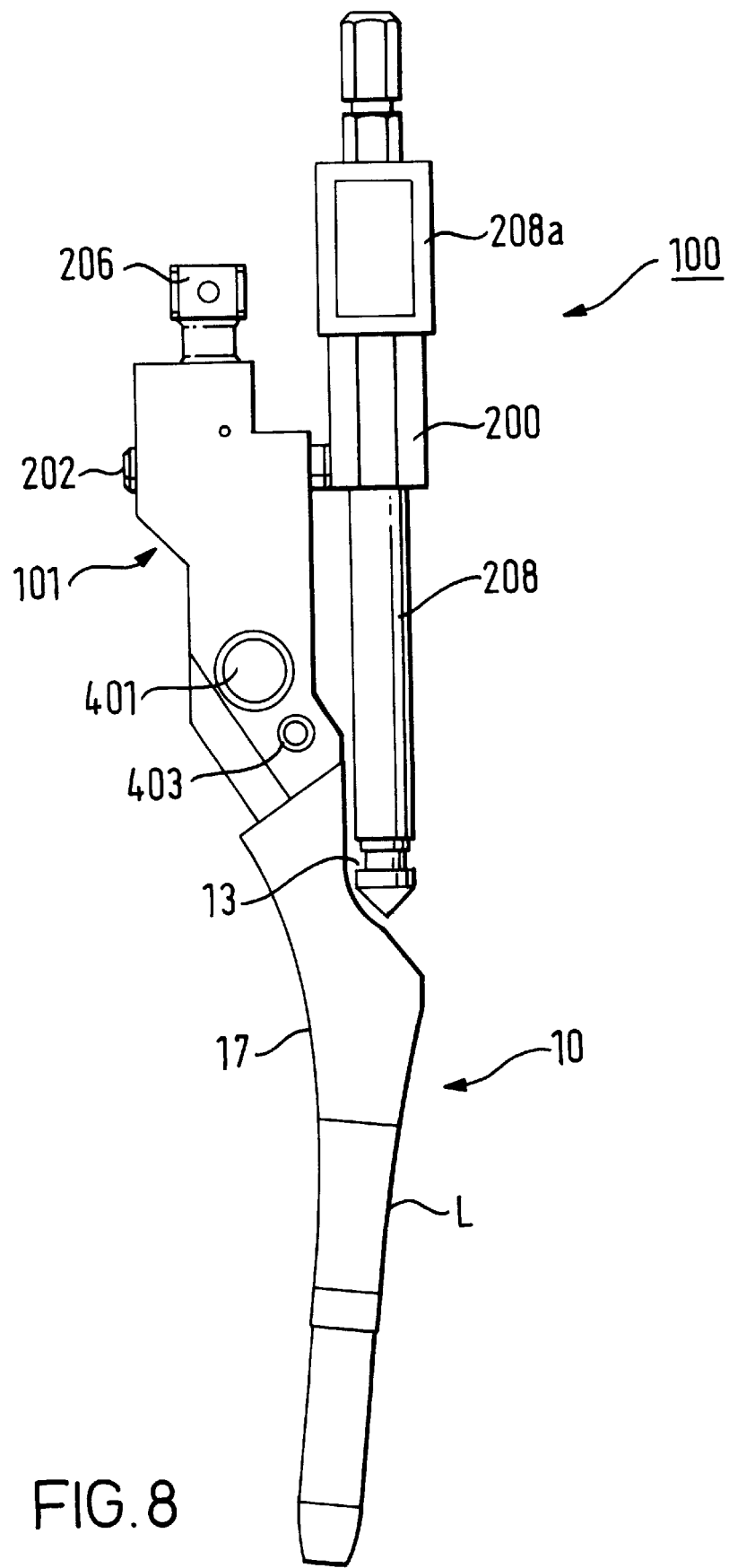
FIG. 8 is an anterior view of the assembled machining assembly, including a cutting instrument and broach.

As illustrated in FIGS. 7–25C, the inventive broach may also be used in combination with a machining device comprising a guide (200) configured to receive a second cutting instrument (208), the latter instrument being designed to machine additional bone initially avoided by the broach. FIG. 8 illustrates the preferred machine assembly comprising, in combination, the inventive broach (10) and a machining device comprising a mounting block (101), a guide (200), and a second cutting instrument (208). Alternatively, the machining assembly could include other types of cutting instruments in instead of the inventive partial broach for insertion within a bone cavity if desired for a particular procedure, including but not limited to, a full broach (e.g. FIG. 3A), rasp, reamer, and the like. Furthermore, other means for securing the guide to the broach, other than a separate mounting block (101) as illustrated and described herein, for example, are within the scope of the present invention. A more detailed description of the specific components of the preferred embodiments of the machining assembly, however, will be discussed further below.

Once the broach has been advanced to the desired position within the medullary canal, a machining device including a guide (200) and a second cutting instrument (208) may be attached to the broach to remove additional bone initially avoided by the broach, as shown in FIG. 8, for example. The shape of the lateral recess (13) of the broach allows the second cutting instrument (208) to be advanced into the cavity (C) to machine away areas of the medial aspect of the greater trochanter (1) to enable insertion of a second broach, such as a finishing broach (not shown), or femoral prosthesis of similar shape as the inventive broach (except for the presence of a lateral recess). Once the second cutting instrument (208) has been advanced within the recess so that all bone is removed, the machining assembly including the broach are removed from the femur. At this point a prosthesis, for example, of suitable shape designed to engage the machined cavity may be implanted in the femur (see FIG. 1, for example). Alternatively, a finishing broach with a shape similar to the inventive broach and the implantation site may be introduced into the femur to generate the final shape of the cavity and to remove discontinuities present between the areas of the femur that were in contact with the inventive broach and machined by the second cutting instrument (208).

The remaining discussion will be directed to the specific components of the preferred machining assembly (100). Referring now to FIGS. 9–18, the machining assembly (100) comprises a guide (200) for receiving and directing the movement of the cutting instrument (208), more preferably including a means for securing the guide to a mounting block (101), and most preferably a means for allowing slidable engagement of the guide within the block (101) to permit multiple cutting positions relative to the block (101). Alternatively, the guide may be permanently attached to the mounting block or even directly to the broach by some other means of attachment. Preferably, the guide (200) comprises a body (201) having an outer surface (201a) and an inner passage (203) communicating therethrough for receiving a second cutting instrument (208).

The second cutting instrument (208) preferably includes a means for limiting the distance it may travel through the guide, preferably a collar (208a) affixed to the upper end of the instrument and which rests on the upper edge of the guide, for example as shown in FIG. 8. In the preferred embodiment, the cutting instrument is a cylindrical reamer which passes through a cylindrically-shaped guide, as illustrated in the figures; however, other means of machining bone are contemplated to be within the scope of the present invention, including, but not limited to, a hollow drill, a bone punch, or a chisel configured to match the shape of the recess.

A preferred second cutting instrument (208) is a 90-degree point cutter as illustrated in FIGS. 24A–24B and 25A–25C. Here, the cutting instrument (208) comprises a body portion having preferably six flutes (211) and a distal tip (212) comprising a total of six cutting edges—two cutting edges (212a) converging into a point at a 90-degree angle (8) and four cutting edges (212b) terminating into a flat plane (212c) perpendicular to the longitudinal axis (Z) of the cutting instrument (208).

Figure 17:
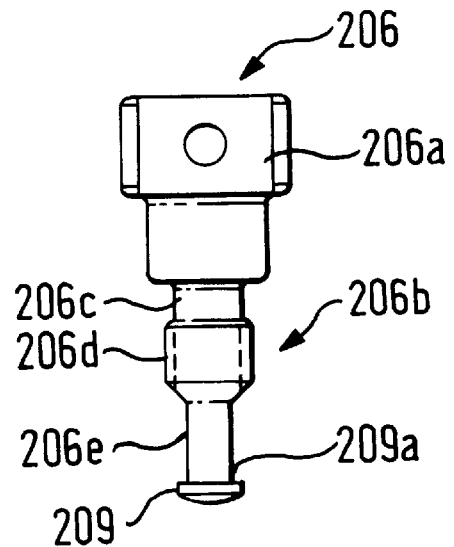
FIG. 17 is an enlarged view of the locking screw for securing the guide to the mounting block.
Figure 18:
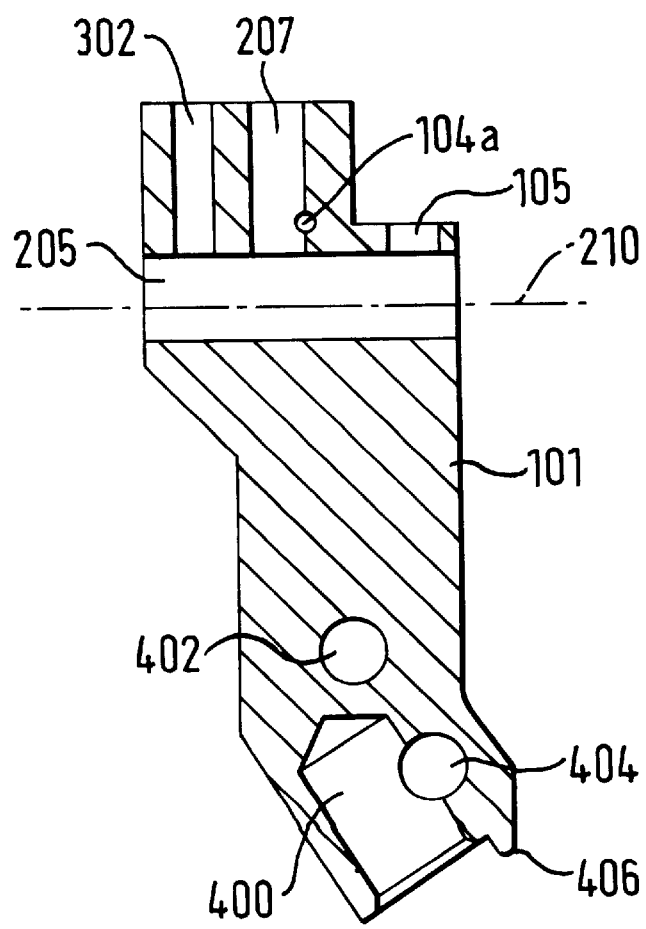
FIG. 18 is a longitudinal cross section view of the mounting block illustrating the various channels and bores.
Figure 19:
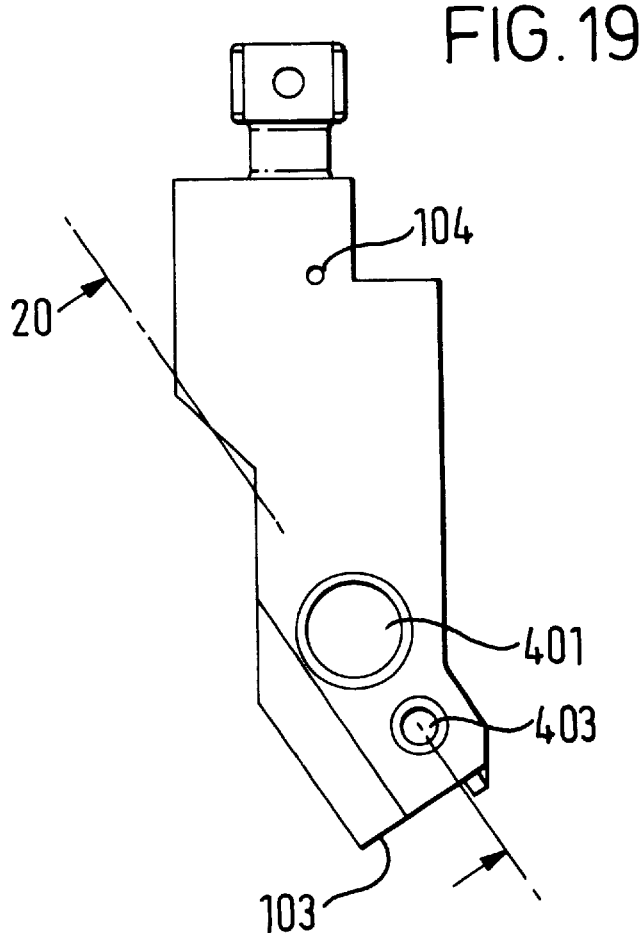
FIG. 19 is a side view of the machining assembly (without the broach and second cutting instrument).
Figure 20:
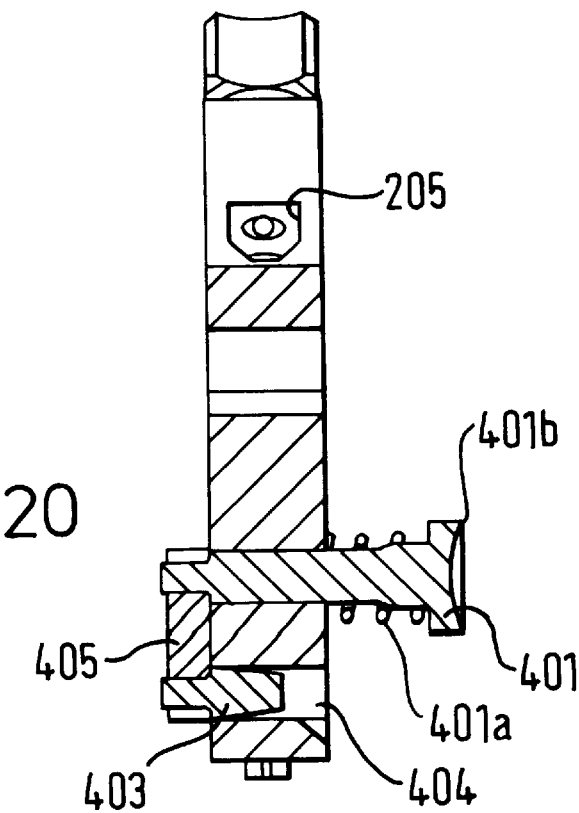
FIG. 20 is a cross section view of the machining assembly taken along lines 20—20 of FIG. 19 illustrating the preferred means for securing the broach to the mounting block.

The guide preferably includes an arm (202) which may be permanently secured to the mounting block; however, in the most preferred embodiment, the guide arm (202) is slidablely engaged within a complementary transverse chamber (205) passing through the block (FIG. 18). In this embodiment, the arm may be adjusted to different positions laterally for a desired cutting area, as discussed above. The machining assembly includes a means for securing the arm (202) within the chamber (205), preferably a locking screw (206) having a head (206a) and a lower body (206b) engaged within a complementary longitudinal bore (207) positioned on the superior end (102) of the block and in the communication with the transverse chamber (205). When the screw head (206a) is turned in one direction, the lower body (206b) of the screw moves downward to contact the guide arm (202) to preclude any further sliding movement of the guide arm within the chamber (205). When the screw head is turned in the opposite direction, the lower body is retracted to release the arm (202), thereby permitting slidable movement of the guide arm within the chamber. FIG. 17 illustrates an enlarged view of a locking screw design, wherein the lower body (206b) is further divided into four segments: a narrow segment (206c) subjacent the screw head (206a); a wide segment (206d) subjacent the narrow segment; an elongated segment (206e) subjacent the wide segment (206d); and a distal tip (209) having a diameter larger than the superior elongated segment (206e). Furthermore, to prevent the locking screw (206) from being disassembled from the mounting block (101) and possibly lost, a grooved pin (104) is employed which is contained within a complementary chamber (104a) communicating through the mounting block (101) adjacent the locking screw (206), as shown in FIGS. 13, 18, and 19, for example. Upon retraction of the locking screw (206), the upper edge (209a) of the lower tip (209) of the screw contacts the grooved pin (104) to prevent further upward movement and subsequent removal of the locking screw from the mounting block (101).

Figure 9:
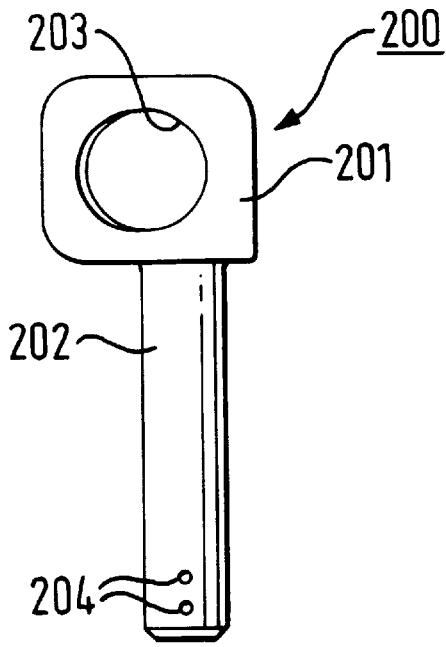
FIGS. 9–11 are front, back, and side views, respectively, of the guide component of the machining assembly.
Figure 10:
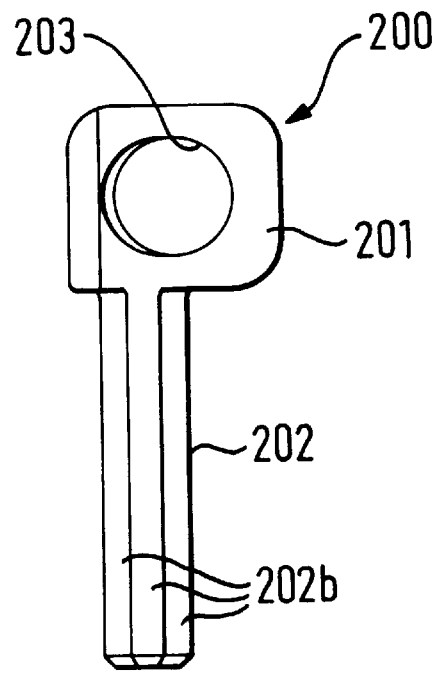
Figure 11:
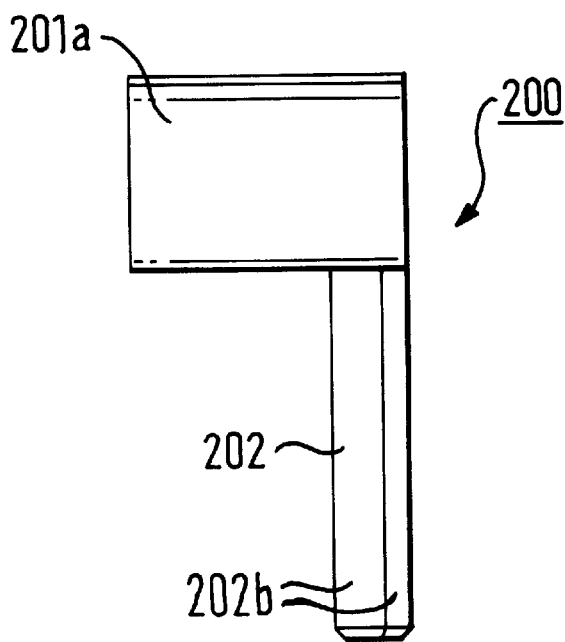
Figure 16:
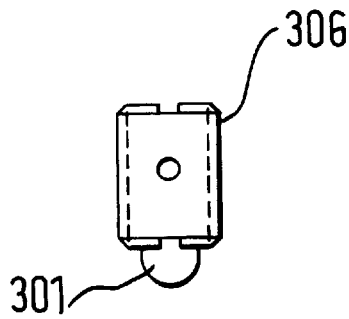
FIG. 16 is an enlarged view of the spring plunger.

Referring specifically to FIGS. 9, 13, 16, and 18, the guide arm (202) preferably includes a means for adjusting the guide at multiple positions relative to the mounting block, most preferably a plurality of indentations (204) positioned on the upper surface of the guide arm, and a spring biased plunger (300) engaged within a complementary longitudinal bore (302) parallel to the locking screw (206) and perpendicular to the transverse chamber (205). The plunger (300) includes a spring loaded lower resilient tip (301) which protrudes into the transverse chamber (205), such that when an indentation (204) is positioned directly beneath the plunger, the lower tip (301) engages the indentation (204). The indentations are spaced apart from each other at desired intervals corresponding to different size broaches that may be employed during the surgical procedure. For example, the guide (200) illustrated in FIGS. 9–11 comprises two indentations spaced apart to correspond to two different broach sizes (i.e. No. 4 and No. 5 broaches). Preferably, the sizes are engraved on the guide arm (202) and can be viewed by the surgeon through an opening (105) in the block. Finally, while guide arms of different configurations may be employed, the preferred configuration is one having at least three flat sides that correspond to a transverse chamber (205) having at least three corresponding sides to prevent rotational movement of the arm about a transverse axis (210) defined within the chamber (205). The most preferred embodiment as illustrated in the figures comprises six sides (202b) arranged as illustrated in FIGS. 9–11 for greater engagement and wear.

Figure 21:
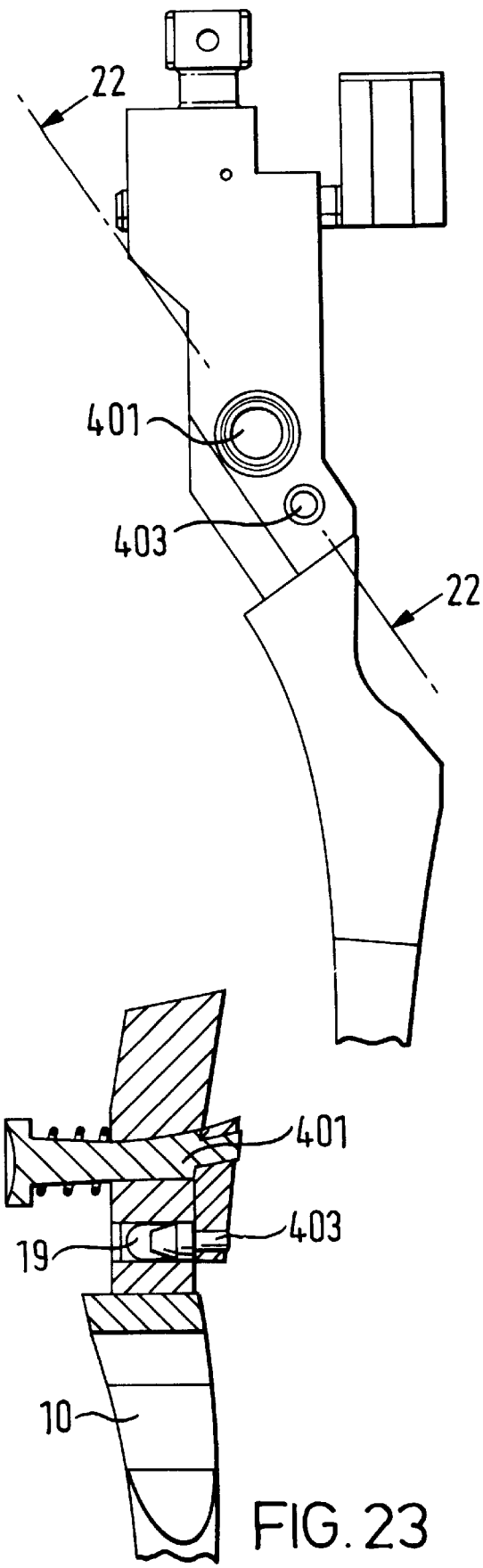
FIG. 21 is a side view of the machining assembly.
Figure 22:
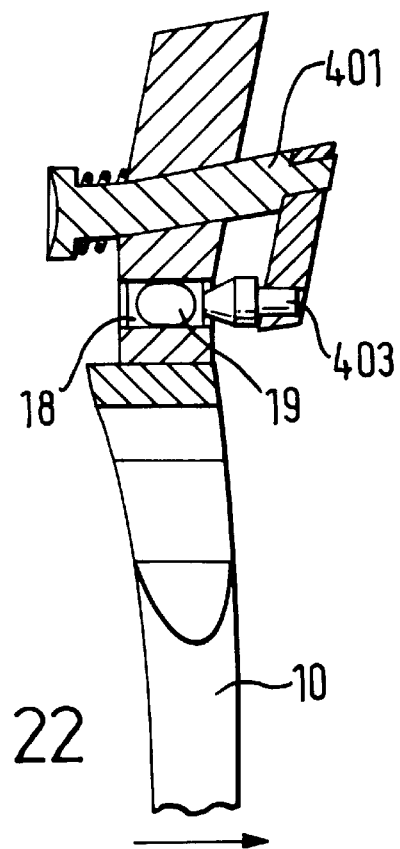
FIG. 22 is a cross-section view of the machining assembly taken along lines 22—22 of FIG. 21, wherein the locking assembly is shown in the home or retracted position to secure the broach within the mounting block.
Figure 23:
FIG. 23 is the cross-section view of the machining assembly as illustrated in FIG. 22, wherein the locking assembly is shown in the open position to allow insertion of the broach within the mounting block.
Figure 25A:
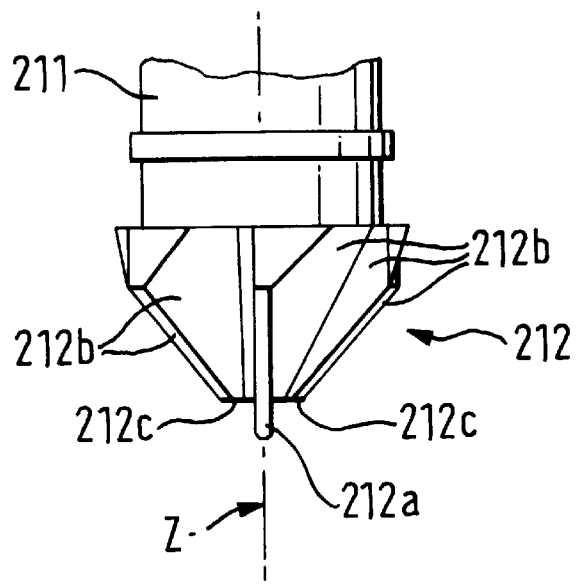
FIG. 25A is an enlarged view of the distal tip of the second cutting instrument illustrated in FIGS. 24A–24B.
Figure 25B:
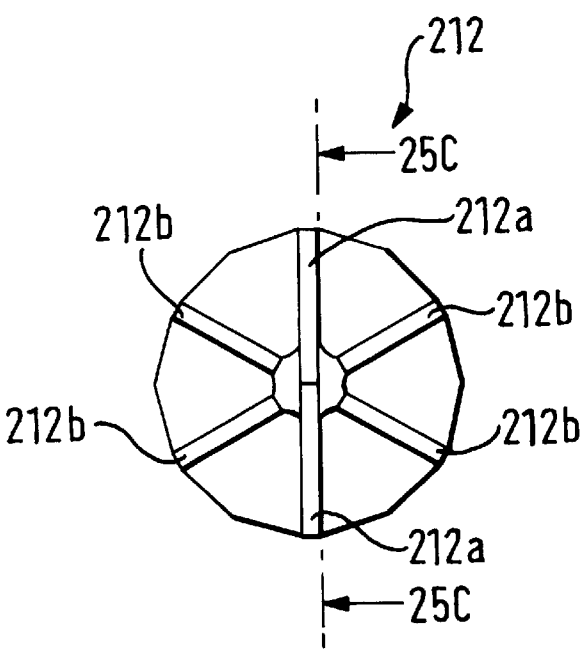
FIG. 25B is a bottom plan view of the second cutting instrument illustrated in FIG. 25B.
Figure 25C:
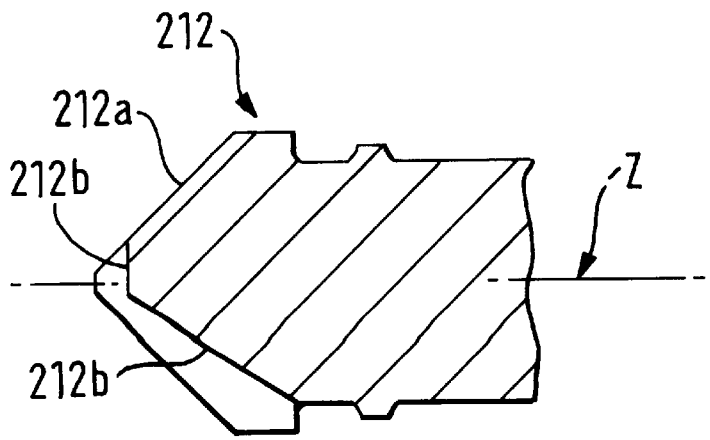
FIG. 25C is a cross-section view of the distal tip taken along lines 25C—25C of FIG. 25B.

Referring now to FIGS. 12–15 and 18–23, the inventive machining assembly (100) further includes a means for securing a broach to the mounting block (101). While other conventional locking means known by those of ordinary skill in the art may be employed, the figures illustrate a preferred locking mechanism which includes a bore (400) present in the inferior end (103) of the block and configured for receiving a boss or trunion (18) positioned on the superior end (12) of the broach. Also carried on the mounting block (101) is a locking pin assembly comprising a spring biased push pin (401) engaged within a first complementary transverse chamber (402) positioned above the bore (400), a locking pin (403) engaged within a second complementary transverse chamber (404) parallel to the first chamber (401) and in communication with the bore (400), wherein the second chamber (404) is positioned between the bore (400) and the first chamber (401), and a connecting piece (405) securing one end of the locking pin (403) to an end of the push pin (401). Preferably, the push pin (401) is housed within a helical spring (401a) having a sufficiently high compression to ensure stability of the locking system. As illustrated in FIGS. 21–23, when the spring pin (401) is actuated (i.e. pushed in the direction of the arrow), the locking pin (403) is disengaged from its corresponding transverse chamber (404) to allow entry of the broach's boss or trunion (18) into the bore (400) (FIG. 22). Upon subsequent release of the push pin (401), the locking pin (403) re-enters the bore (400) to lock the boss (18) therein, thereby securing the broach to the mounting block (101) (FIG. 23). Preferably, the locking pin (403) is tapered to slide into, and be received by, a corresponding notch (19) positioned on the trunion or boss (18). For additional stability, the mounting block may also include a small key member (406) (FIGS. 14–15 and 18) that extends downward below the bore (400) and is configured to engage a complementary groove (20) positioned on the superior end (13) of the broach adjacent the boss (18), as illustrated in FIG. 5, for example. Engagement of the key member (406) within the groove (20) functions to prevent any rotational movement of the mounting block (101) about the longitudinal axis (X) of the broach (10).

The present invention is particularly advantageous in the preparation of a femoral medullary cavity for receipt of a femoral prosthesis whereby upon subsequent implantation of the prosthesis, the longitudinal axis of the prosthesis substantially coincides with the medullary axis, thereby achieving neutral alignment within the cavity for more rigid fixation and stability. One method of preparing the desired implantation site is to drive the partial broach into the medullary cavity as described above in Section II. Once the medullary cavity has been prepared using the partial broach, a second finishing broach that does not contain a lateral recess may then be used to enlarge the implantation site to its final shape as well as remove bone in the medial aspect of the greater trochanter. In the most preferred embodiment, however, the inventive machining assembly as described herein is employed in combination with, or in lieu of, the second finishing broach, at least with respect to removal of bone from the greater trochanteric region of the femur. FIG. 7 illustrates the machining assembly (100) implanted within the medullary cavity (C) of a femur (F). Here, once the broach is implanted into the medullary cavity at the desired location, the mounting block (101) comprising the guide (200) and second cutting instrument (208) is secured to the trunion (18) by means of the locking pin assembly described above. The guide is then secured within the transverse chamber (205) and placed laterally over the recessed area (13) of the broach (10) at a position corresponding to the desired broach size. The second cutting instrument (208) is then placed within the guide and advanced into the recessed cavity, preferably by means of a straight plunge, to machine away areas of the medial aspect of the greater trochanter to enable insertion of another broach or prosthesis of similar shape to the inventive partial broach (but without having the lateral recess). Once the second cutting instrument (208) is advanced to the distal portion of the recess, the cutting instrument (208) may be withdrawn from the recess, the guide transferred to a new position, and then the cutting instrument (208) is again advanced to the maximum possible depth (i.e. the distal portion of the recess). This process may be repeated until all bone within the recess has been removed. Alternatively, a side cutting reamer (not shown) may be advanced through the guide and then moved along a curved track in a side-cutting manner until all bone has been removed.

For ease of explanation, the description of the design and use of the inventive machining assembly has been confined to the preferred method of use, namely in preparing the femoral medullary cavity to receive a femoral prosthesis during hip arthroplasty. As discussed above, when the machining assembly includes the inventive partial broach described herein, it possible to prepare a medullary cavity that allows for the subsequent implantation of a neutrally aligned femoral stem component. It is contemplated, however, that one of ordinary skill in the art, having the benefit of the invention's teachings and suggestions, could make any necessary modifications to the machining assembly, including the broach, for other orthopedic surgical procedures requiring the removal of bone.

The preferred materials for fabricating the components of the machining assembly, including the inventive broach, are those typically employed in orthopedic surgical instruments and implants, including, but not limited to, stainless steels and alloys of cobalt, chromium, and molybdenum. Preferred materials include 455 and 17-4 precipitated hardenable stainless steels. For optimal results, the outer surface of the second cutting instrument employed within the guide is preferably electropolished and coated with a chromium nitride or similar surface hardening compound.

The foregoing disclosure and description of the invention are illustrative and explanatory thereof, and various changes in the size, shape, and materials, as well as in the details of the illustrated construction, including, but not limited to, modifications necessary to accommodate variations in patient anatomy, may be made without departing from the spirit of the invention.

I claim:

1. A broach suitable for preparing a medullary cavity of a femur for subsequent implantation of a prosthetic stem, said broach comprising:

a longitudinal axis;

anterior, posterior, medial, and lateral faces;

a plurality of cutting teeth positioned on at least one of said faces; and a proximal segment including said faces and having a superior end; and a recess positioned on said lateral face of said proximal segment, said recess comprising a medial portion and a distal portion, wherein said medial portion is spaced medially from said lateral face and extends distally from said superior end to said distal portion, and said distal portion extends laterally from said medial portion to said lateral face.

2. The broach of claim 1, wherein said recess extends from said posterior face to said anterior face of said broach.

3. The broach of claim 2, wherein said distal portion of said recess further includes a lateral edge and a chamfer extending distally from said lateral edge.

4. A method for implanting a femoral prosthesis into a femur, said method comprising the steps of:

(a) preparing a site for implantation of a prosthesis within a femoral medullary cavity by first driving a broach into the medullary cavity until said broach is in neutral alignment within said cavity, wherein said broach comprises a longitudinal axis; anterior, posterior, medial, and lateral faces; a plurality of cutting teeth positioned on at least one of said faces; a proximal segment including said faces and having a superior end; and a recess positioned on said lateral face of said proximal segment said recess comprising a medial portion and a distal portion, wherein said medial portion is spaced medially from said lateral face and extends distally from said superior end to said distal portion, and said distal portion extends laterally from said medial portion to said lateral face;

(b) removing said broach from said implantation site;

(c) removing a sufficient amount of greater trochanteric bone from said femur with a second cutting instrument to allow passage of a femoral prosthesis into the prepared implantation site, said prosthesis having a longitudinal axis; and (d) implanting said femoral prosthesis into the prepared implantation site within said medullary cavity, wherein the longitudinal axis of said prosthesis substantially coincides with the medullary axis for neutral alignment of the prosthesis therein.

5. The method of claim 4, wherein said second cutting instrument is a finishing broach having a plurality of cutting teeth.

6. The method of claim 4, wherein the recess of said broach further extends from said proximal face to said anterior face.

7. The method of claim 4, wherein said distal portion of said recess further includes a lateral edge and a chamfer extending distally from said lateral edge.

* * * * *